United States Patent
De Figueiredo Portilho et al.

(10) Patent No.: US 12,071,400 B2
(45) Date of Patent: Aug. 27, 2024

(54) PROCESS OF SELECTIVE OXIDATION OF GLYCEROL

(71) Applicants: PETRÓLEO BRASILEIRO S.A.-PETROBRAS, Rio de Janeiro (BR); UNIVERSIDADE FEDERAL DE MINAS GERAIS-UFMG, Belo Horizonte (BR)

(72) Inventors: Marcio De Figueiredo Portilho, Rio de Janeiro (BR); Victor Augusto Araujo De Freitas, Belo Horizonte (BR); Luiz Carlos Alves De Oliveira, Belo Horizonte (BR)

(73) Assignees: PETRÓLEO BRASILEIRO S.A.—PETROBRAS, Rio de Janeiro (BR); UNIVERSIDADE FEDERAL DE MINAS GERAIS—UFMG, Belo Horizonte (BR)

(*) Notice: Subject to any disclaimer, the term of this patent is extended or adjusted under 35 U.S.C. 154(b) by 684 days.

(21) Appl. No.: 17/293,209

(22) PCT Filed: Nov. 12, 2019

(86) PCT No.: PCT/BR2019/050488
§ 371 (c)(1),
(2) Date: May 12, 2021

(87) PCT Pub. No.: WO2020/097707
PCT Pub. Date: May 22, 2020

(65) Prior Publication Data
US 2022/0009871 A1 Jan. 13, 2022

(30) Foreign Application Priority Data
Nov. 13, 2018 (BR) .................. 102018073404-0

(51) Int. Cl.
*C07C 51/245* (2006.01)
*B01J 8/02* (2006.01)
(Continued)

(52) U.S. Cl.
CPC .............. *C07C 51/245* (2013.01); *B01J 8/02* (2013.01); *B01J 8/24* (2013.01); *B01J 21/04* (2013.01);
(Continued)

(58) Field of Classification Search
CPC .... B01D 3/14; B01D 5/00; B01J 21/04; B01J 21/08; B01J 23/745; B01J 8/02;
(Continued)

(56) References Cited

PUBLICATIONS

Wang et al. (Catalytic Oxidative Dehydration of Glycerol over a Catalyst with Iron Oxide Domains Embedded in an Iron Orthovanadate Phase, ChemSusChem, 3, 1383-1389, Published 2010) (Year: 2010).*

* cited by examiner

*Primary Examiner* — Yevgeny Valenrod
*Assistant Examiner* — Blaine G Doletski
(74) *Attorney, Agent, or Firm* — Birch, Stewart, Kolasch & Birch, LLP (57) ABSTRACT

The present invention describes a selective glycerol oxidation process comprising a set of steps. In the first step, a glycerol-containing raw material and an oxidizing agent are fed into a reaction vessel containing an iron oxide-containing catalyst. Subsequently, the glycerol-containing raw material, the oxidizing agent, and said iron oxide-containing catalyst are brought into contact at a temperature in the range of 100 to 350° C., wherein the glycerol-oxidation reaction occurs.

18 Claims, 7 Drawing Sheets

(51) Int. Cl.
  *B01J 8/24*    (2006.01)
  *B01J 21/04*   (2006.01)
  *B01J 21/08*   (2006.01)
  *B01J 23/745*  (2006.01)
  *C07C 51/44*   (2006.01)
  *B01D 3/14*   (2006.01)
  *B01D 5/00*   (2006.01)

(52) U.S. Cl.
  CPC ............ *B01J 21/08* (2013.01); *B01J 23/745* (2013.01); *C07C 51/44* (2013.01); *B01D 3/14* (2013.01); *B01D 5/00* (2013.01)

(58) Field of Classification Search
  CPC .. B01J 8/24; B01J 35/30; B01J 35/393; C07C 51/245; C07C 51/285; C07C 51/44; C07C 51/23; C07C 51/34; C07C 53/02; G01L 13/02; G01L 19/0007; G01L 19/06; G01L 7/08
  See application file for complete search history.

PROCESS OF SELECTIVE OXIDATION OF GLYCEROL

FIELD OF THE INVENTION

The present invention is related to a selective glycerol oxidation process. More specifically, the present invention suggests the use of catalysts containing iron oxide in a selective glycerol oxidation process.

BACKGROUND OF THE INVENTION

The need to reduce emissions of gaseous pollutants, such as $CO_2$, and the search for lower use of non-renewable energy matrices (due to fluctuations in the international price of oil) result in a continuous increase in demand for liquid biofuels.

In first-generation renewable fuels, such as bioethanol and biodiesel, co-products such as solid waste and glycerol are inevitable in their synthesis processes. Therefore, in a scenario of continuously increasing production, strategies should be employed that make the best use of this waste so that the biofuel production chain becomes more profitable and has minimal waste generation, thus becoming more attractive.

Specifically in the case of biodiesel, co-produced glycerol is used, for example, in drugs, personal care products and products for the home. However, since the glycerol obtained from the chemical biodiesel route—known as crude glycerin—contains several impurities such as salts, di- and monoglycerides and other organic materials, it must be treated and purified in order to meet market specifications.

Since these treatment and purification processes have an associated additional cost, they are often inaccessible to small- and medium-sized biodiesel producers, since the market price of the purified co-product does not generate enough revenue to offset all costs associated with the glycerin-purification steps.

Furthermore, despite the fact that crude glycerin has its own market value, its abundant supply, due to increased domestic biodiesel production in recent years, has resulted in a drop in its price, thus selling it directly is not financially advantageous.

Considering this scenario, the need to develop processes that are capable of converting crude glycerin resulting from biodiesel into products of greater added value, without the need for pre-treatment or purification of this raw material, is evident.

In the conversion processes, the molecular structure of glycerol allows this compound to undergo various reactions such as, for example, oxidation, hydrogenolysis, dehydration, acetylization, carboxylation, pyrolysis, gasification and deoxygenation.

Oxidation reactions are particularly relevant, since the products resulting from this route are of interest to the petrochemical industry, and although this route is complex and leads to the formation of several products, there is the advantage that practically all the resulting oxygenated derivatives have practical applications.

Among the possible products from oxidation, formic acid has shown particular relevance because it is a chemical commodity that is of substantial interest within the context of clean energy generation as a safe alternative for hydrogen storage.

Oxidation of glycerol can be mediated by low-cost catalysts and oxidizing agents such as air, oxygen and hydrogen peroxide. The supported catalysts most commonly found for this purpose are comprised of noble metals such as palladium, platinum, gold, rhenium and ruthenium, supported on silica, alumina or activated carbon.

However, it should be noted that these catalysts are mostly used in reactions with refined or pure glycerin, and that the use of noble metals in the catalyst implies disadvantages such as the high cost associated with its production, and in the case of platinum, the poisoning of the catalyst at high partial pressures of oxygen, which require constant catalytic reactivation processes.

An alternative to noble metal-based catalysts was proposed in the study by Oliveira, H. ("*Conversão de glicerina residual do biodiesel em ácido fórmico utilizando catalisadores de nióbio e vanádio*" [*Conversion of residual biodiesel glycerin into formic acid using niobium and vanadium catalysts*], 2016. 109f. Thesis (PhD in Chemistry)—Institute of Exact Sciences, Federal University of Minas Gerais, Belo Horizonte, 2016), in which niobium and vanadium oxides are impregnated in catalytic supports. The synthesized catalysts are used in the selective oxidation of glycerin. However, it can be seen that such oxides do not show very high catalytic activity, requiring impregnation with high content of niobium and vanadium oxides in the supports; additionally there is little difference in selectivity between formic acid and other majority products such as dioxanes.

A more accessible alternative to noble metal-based catalysts are iron-based catalysts. Such catalysts are used in other technical areas, as described in patent document CN104096570, where catalysts impregnated with metallic iron are synthesized and used to produce lower carbon chain olefins by means of Fischer-Tropsch synthesis.

In the technical area associated with the present invention, the study "*Selective oxidation of glycerol catalyzed by iron complexes*" (FARNETTI, E. and CROTTI, C., *Catalysis Communications*, 2016 84, 1-4) describes the use of iron complexes (III) and iron (II) in glycerol oxidation using homogeneous catalysis. Although the study generated formic acid together with dioxanes, in terms of selectivity, the production of dioxane dihydroxyacetone and formic acid are practically equal, thus this catalysis is not selective for any of the said compounds. Furthermore, this process has several disadvantages associated with the use of homogeneous catalysis, such as, for example, the need for additional catalyst separation steps for its reuse, which decreases the economic efficiency of the process.

It is therefore noted that the state of the art lacks an effectively selective method for producing formic acid from glycerol that uses catalysts with easy operability, capable of being used regardless of the degree of purity of the glycerol and for longer campaign times.

It is therefore necessary to develop a process that can process raw materials containing glycerol of varying degrees of purity—from crude glycerin to purified glycerol—and that can produce formic acid selectively and economically so that the problems encountered in the state of the technique are resolved.

SUMMARY OF THE INVENTION

The present invention is related to a selective glycerol oxidation process that uses an iron oxide-based catalyst in heterogeneous catalysis.

A first objective according to the present invention is to generate glycerol oxidation products selectively, using a catalyst that is easily operable and capable of acting for longer campaign times.

A second objective according to the present invention is to process raw materials containing glycerol of varying degrees of purity—from crude glycerin to purified glycerol—generating formic acid selectively and economically.

In order to achieve the objectives described above, the present invention seeks to perform a process comprising a set of steps, where, in the first step, a raw material containing glycerol and an oxidizing agent are fed into a reaction vessel containing a catalyst comprising iron oxide. Subsequently, the raw material containing glycerol, the oxidizing agent, and said iron oxide-containing catalyst are brought into contact at a temperature in the range of 100 to 350° C., causing the glycerol oxidation reaction, which results in an oxidized mixture.

The process in accordance with the present invention reduces the relative costs of purifying the glycerol oxidation products, since it uses heterogeneous catalysis and does not require further steps to remove the catalyst from the reaction medium, making said products thus produced competitive against the products traditionally generated from oil.

These objectives and other advantages of the present invention will become more evident from the following description and the accompanying drawings.

BRIEF DESCRIPTION OF THE DRAWINGS

The following detailed description references the attached figures.

DETAILED DESCRIPTION OF THE INVENTION

The present invention relates to a selective glycerol oxidation process mediated by an iron oxide-containing catalyst.

The process of the present invention suggests, first, that a raw material containing glycerol and an oxidizing agent be fed into a reaction vessel containing an iron oxide-containing catalyst. Subsequently, the raw material containing glycerol, the oxidizing agent, and the iron oxide-containing catalyst are brought into contact at a temperature in the range of 100 to 350° C., with the advantage that the glycerol will be selectively oxidized to a specific oxidation product. In preferred embodiments, the temperature at which the glycerol-containing raw material, the oxidizing agent, and the iron oxide-containing catalyst are brought into contact is in the range of 150 to 250° C.

Within the scope of the present invention, the term "selectively oxidized" and its variants refer to the fact that the mixture resulting from the selective glycerol oxidation process, here called the oxidized mixture, has a majority product in its composition. It is important to note that this oxidized mixture may comprise not only the products from the oxidation reaction, but also possible reagents and/or remaining impurities derived from the glycerol-containing raw material.

Specifically, this majority product refers to the product that is in greater proportion by weight in the resulting oxidized mixture, based on the sum of the weights of all products resulting from the oxidation of glycerol, excluding the weight of possible reagents and/or remaining impurities.

In preferred embodiments of the present invention the majority product of the oxidized mixture is formic acid. In even more preferred embodiments, the content of formic acid in the oxidized mixture is within the range of 40 to 90% by weight, based on the sum of the weights of oxidation products contained in the oxidized mixture. It should be noted that this concentration range is not a limiting factor of this embodiment of the invention, as it is only necessary that formic acid be the product with the highest concentration by weight among all the other oxidation products present in the oxidized mixture.

The term "oxidation products" refers to all compounds resulting from the oxidation reaction of the glycerol-containing raw material present in the oxidized mixture, excluding the remaining glycerol and oxidizing agent. Possible inert impurities in the glycerol-containing raw material (such as, for example, sodium chloride and other matter organic non-glycerol—MONG) or in the oxidizing agent are also not considered.

The term "reaction vessel," into which the glycerol-containing raw material and the oxidizing agent are fed, refers to any empty container, either closed or open, in which a chemical reaction is possible, which vessel may be manufactured of any material, such as plastics, glass, metals, metal alloys and ceramic, whether or not it is coated with other materials.

The glycerol-containing raw material is not limited only to the glycerol itself or to its aqueous solutions; several other raw materials whose composition contains glycerol can be used, for example, crude glycerin, desalinated glycerin, and blonde glycerin. The glycerol content in said glycerol-containing raw material is in the range of 30 to 100% by weight. In another embodiment, the glycerol content in said glycerol-containing raw material is in the range of 30 to 80% by weight. Lower levels may be used if the glycerol-containing raw materials are additionally diluted, regardless of the solvent to be used in said dilution.

The oxidizing agent fed into the reaction vessel consists of a fluid in liquid or gaseous phase, containing a substance capable of causing oxidation of the glycerol present in the glycerol-containing raw material. The oxidizing agent to be used in the present invention is preferably selected from the group consisting of oxygen, hydrogen peroxide, and ozone. More preferably, hydrogen peroxide is used as the oxidizing agent.

Such oxidizing agents are not limited to their use in pure form, but may be represented by oxidizing solutions of the listed compounds. The term "oxygen" may refer both to the compound in its pure form, and to its solutions, for example, air and air-oxygen mixtures, in any proportion. In preferred embodiments, the air-oxygen mixture is formed by an air:oxygen ratio in the range of 1:1 to 10:1 by volume.

The same understanding given to the term "oxygen" applies to the term "ozone," and this oxidizing agent can be an air-ozone mixture in any proportion, preferably in an air:ozone ratio in the range of 1:1 to 10:1 by volume.

The term "hydrogen peroxide" may also refer to oxidizing solutions of this compound, represented, for example, by aqueous solutions in hydrogen peroxide concentrations from 10 to 80% v/v, based on the total volume of the solution. In preferred embodiments, a hydrogen peroxide solution in concentrations ranging from 10 to 50% v/v is used, based on the total volume of the solution.

Preferably, the oxidizing agent to be used is hydrogen peroxide or its solutions.

Although the oxidation process of glycerol-containing raw material essentially comprises the steps listed above, prior and subsequent steps may optionally be carried out.

Optionally, the glycerol-containing raw material and the oxidizing agent may be mixed before being fed into the reaction vessel. This step may be advantageous, for example, when the glycerol-containing raw material and the oxidizing agent are present in the same physical state, thus enabling greater homogeneity and better distribution between the reagents when fed into the reaction vessel, preventing operational problems associated with weight transfer.

In principle, the glycerol-containing raw material and the oxidizing agent can be fed into the reaction vessel in any volumetric proportion. Preferably, the glycerol-containing raw material and the oxidizing agent are fed into the reaction vessel in a volume ratio of (glycerol-containing raw material):(oxidizing agent) in the range of 1:1 to 1:5. If the step of mixing the glycerol-containing raw material with the oxidizing agent is carried out before they are fed into the reaction vessel, said mixing is preferably carried out in a volume ratio of (glycerol-containing raw material):(oxidizing agent), also in the range of 1:1 to 1:5.

In an optional embodiment of the present invention, the oxidized mixture resulting from the oxidation process of glycerol-containing raw material undergoes a step (c) of recovery of oxidation products. Preferably, the recovery of the oxidation products occurs through a process selected from simple distillation, fractional distillation, simple condensation, fractional condensation, or a combination thereof.

The step of recovering oxidation products through simple condensation of the oxidized mixture may be carried out at any temperature below the dew point of the oxidized mixture at atmospheric pressure. In preferred embodiments of the present invention, the simple condensation recovery step is carried out at a temperature between 0 and 25° C.

If fractional condensation is used, the temperatures at which condensation occurs will depend on the substances of interest to be separated. In preferred embodiments, a first stage of fractional condensation seeks to condense water and other compounds with a higher boiling point. In subsequent condensation steps, the oxidation products of interest are recovered.

Another optional embodiment of the oxidation process of the present invention comprises a pre-treatment step of the glycerol-containing raw material. This optional step is carried out before the reaction vessel is fed, or even prior to the step of mixing the glycerol-containing raw material with the oxidizing agent, if that step is done. This pre-treatment step seeks to increase the glycerol purity of the glycerol-containing raw material, and it is preferably selected from the group consisting of hydrolysis, filtration, physisorption, chemisorption, distillation, decantation, neutralization, refining, or combinations thereto.

Naturally, pre-treatment of the physisorption is entirely optional, since the technical effects of the present invention are obtained regardless of the degree of purity of this raw material, while the decision of whether or not to employ this step is fully at the discretion of the operator, depending on the desired specifications of the reagent and the product.

The oxidation process of glycerol-containing raw material of the present invention is not limited to a single conduction regime, but may be carried out in batch, semi-batch or continuous regimes. In preferred embodiments, the process is carried out continuously.

If the oxidation process of glycerol-containing raw material is carried out in a continuous regime, it is advantageous to determine the entry of reagents using weight hour space velocity (WHSV). This parameter, widely known in the state of the art, is defined with the ratio between the weight flow of the reagents fed into the reaction vessel and the catalyst weight contained in the reaction vessel. Preferably, the process is performed under weight hour space velocity (WHSV) in the range of 0.5 to 10 $h^{-1}$, more preferably in the range of 1 to 5 $h^{-1}$.

In addition, when the process is performed in a continuous regime, the reaction vessel used in the process is preferably selected from the group consisting of a fixed bed reactor, fluidized bed reactor, and mud bed reactor, although it is not limited to these specific types of reaction vessels.

In order to obtain the advantageous technical effects associated with the process of the present invention, it is of paramount importance that the catalyst used be capable of selectively oxidizing the glycerol. The iron oxide-containing catalyst that is used, its synthesis process, and the associated advantages will be described in greater detail.

The iron oxide-containing catalyst used in the process of the present invention is a supported catalyst impregnated with iron oxide. In preferred embodiments, iron oxide is dispersed in a catalytic support selected from the group consisting of silica, alumina, activated carbon, diatomaceous earth, pumice, and zeolite. Most preferably, the catalytic support is selected between silica and alumina.

The synthesis process of the iron oxide-containing catalyst comprises the following steps:
 (a) adding a ferric ion precursor solution to a catalytic support, forming an initial mixture;
 (b) stirring the initial mixture resulting from step (a) under heat until complete evaporation of the solvent contained in the ferric ion precursor solution, forming a dry material;
 (c) mechanically reducing the average particle size of dry material resulting from step (b), forming a reduced dry material;
 (d) calcining the reduced dry material resulting from step (c) in an oxidizing atmosphere.

Preferably, the ferric ion precursor solution consists of an aqueous solution of one of the salts selected from the group consisting of ferric sulfate, ferric nitrate, and ferric carbonate, which may be anhydrous or hydrated.

The amount of ferric ions to be added to the support is defined based on the desired proportion between the ferric ion mass and the support mass contained in the initial mixture. The concentration and volume of ferric ion precursor solution to be added to the support is therefore not a limiting parameter, since there are infinite possible combinations of such parameters capable of reaching the desired mass proportions.

Naturally, for the catalyst to be synthesized properly, it is necessary that the volume of ferric ion precursor solution added is capable of at least filling all the pores of the support used. Thus the use of precursor solutions that are too concentrated is impossible, which limiting factor is common knowledge to a technician in the subject.

In preferred embodiments, the ferric ion solution is added to the support in a proportion in the range of 5 to 20% ferric ions, based on the support mass present in the initial mixture.

Heating in the solvent evaporation step may be done at any temperature capable of causing the solvent to evaporate from the ferric ion precursor solution. In preferred embodiments, said heating is carried out in the range of 50 to 130° C.

The step of reducing the average particle size of dry material consists of any mechanical impact process capable of comminuting the dry material resulting from the evaporation step, such as, for example, crushing or maceration.

Calcination of the reduced dry material is preferably carried out at a temperature in the range of 400 to 600° C. In preferred embodiments, the calcination step is performed for a period of between 3 and 7 hours.

At the end of the synthesis process described above, a catalyst is obtained that contains iron oxide that is highly dispersed in the support, with the size of the iron oxide nanocrystals being formed in the support in the range of 10 to 60 nm. The crystalline phase of the iron oxide, if present, and the size of the nanoparticles dispersed in the support can be analyzed, respectively, by X-ray diffraction (XRD) and energy filtration transmission electron microscopy (EF-TEM).

Dispersal of the iron oxide in the support is a crucial feature in relation to the dual functionality of the catalyst, which must dehydrate and oxidize the glycerol and its intermediates in order to convert glycerol into formic acid, preferably.

Additional analysis of the iron oxide-containing catalyst may optionally be performed to obtain parameters relevant to its characterization, for example, determination of specific area by adsorption of $N_2$ and determination of acidic sites by adsorption of pyridine, by thermogravimetric analysis, and by Tourier-transform infrared spectroscopy (FTIR).

Analysis of the acidic sites of the catalysts resulting from the synthesis process described herein is particularly relevant within the scope of the glycerol oxidation process, since the selectivity to formic acid is proportional to the acidity of the catalyst, that is, the amount of active acidic sites available.

The iron content contained in the iron oxide-containing catalyst is related to the proportion of ferric ions added to the support in the initial step of the catalyst synthesis process. In preferred embodiments, the iron content by weight in the catalyst is in the range of 1 to 20% by weight, based on the total weight of the catalyst. More preferably, said iron content in the iron oxide-containing catalyst is in the range of 3 to 15% by weight.

Naturally, bearing in mind that the impregnation of ferric ions in the catalytic support may not be 100% efficient, it is possible to obtain iron content that is lower than what was added to the support in the catalyst synthesis step.

After the synthesis process, the iron oxide-containing catalyst can be used in the oxidation process of glycerol-containing raw material, with both its concentrated (pure) form and diluted form in inert solid diluent being present in the reaction vessel, in order to have heterogeneous catalysis.

Bearing in mind that oxidation reactions are exothermic, dilution of the iron oxide-containing catalyst may be considered advantageous in instances in which it is more difficult to control temperature due to deficient heat transfer. The dilution of the catalytic bed may therefore prevent the formation of hot spots, thus promoting greater temperature uniformity in the reaction vessel and even extending the useful life of the catalyst.

The term "concentrated form" thus refers to the use of the catalyst without diluents, and it is used in the reaction vessel without mixing it with any inert solid diluent.

The term "inert solid diluent" refers to any comminuted solid material that does not undergo or perform a chemical reaction in the presence of glycerol-containing raw material and/or an oxidizing agent and/or an iron oxide-containing catalyst used in the oxidation process of the present invention.

In preferred embodiments, the iron oxide-containing catalyst is previously diluted in an inert solid diluent in a volume ratio of catalyst:diluent in the range of 1:1 to 1:20. Said inert solid diluent is preferably selected from the group consisting of silica, alumina, silicon carbide, glass spheres, quartz chips, activated carbon, and pumice.

The following description will start with preferred embodiments of the invention based on illustrative examples. As will be evident to any technician skilled in the art, the invention is not limited to these particular embodiments, since they are presented with the sole intention of facilitating the understanding of the characteristics described herein.

EXAMPLES

Example 1—Synthesis of Silica-Supported Iron Oxide-Containing Catalyst ($FeO/SiO_2$)

A silica-supported iron oxide-containing catalyst was obtained using a high-specific area silica support, synthesized in accordance with common practice in the state of the art. 10 ml of a 1.25 mol/L aqueous solution of Fe $(NO_3)_3 \cdot H_2O$ was added to 5 g of the silica support and the resulting mixture was stirred magnetically under heat at 80° C. until complete evaporation of the solvent. The dry material was crushed and calcined at 550° C. for 5 h.

Example 2—Synthesis of Alumina-Supported Iron Oxide-Containing Catalyst ($FeO/Al_2O_3$)

The alumina-supported iron oxide-containing catalyst was obtained using Sasol Pural alumina support. A total of 10 mL of a 1.25 mol/L aqueous solution of Fe $(NO_3)_3 \cdot H_2O$ was added to 5 g of the alumina support and the resulting mixture was stirred magnetically under heat at 80° C. until complete evaporation of the solvent. The dry material was crushed and calcined at 550° C. for 5 h.

Example 3—Characterization by Transmission Electron Microscopy (TEM)

The synthesized catalysts in examples 1 and 2 were characterized by transmission electron microscopy (TEM)

Tecnai G2-20, SuperTwin FEI 200 kV. The images were obtained in filtered FeK α mode and are shown in FIG. 1.

Figure 1:
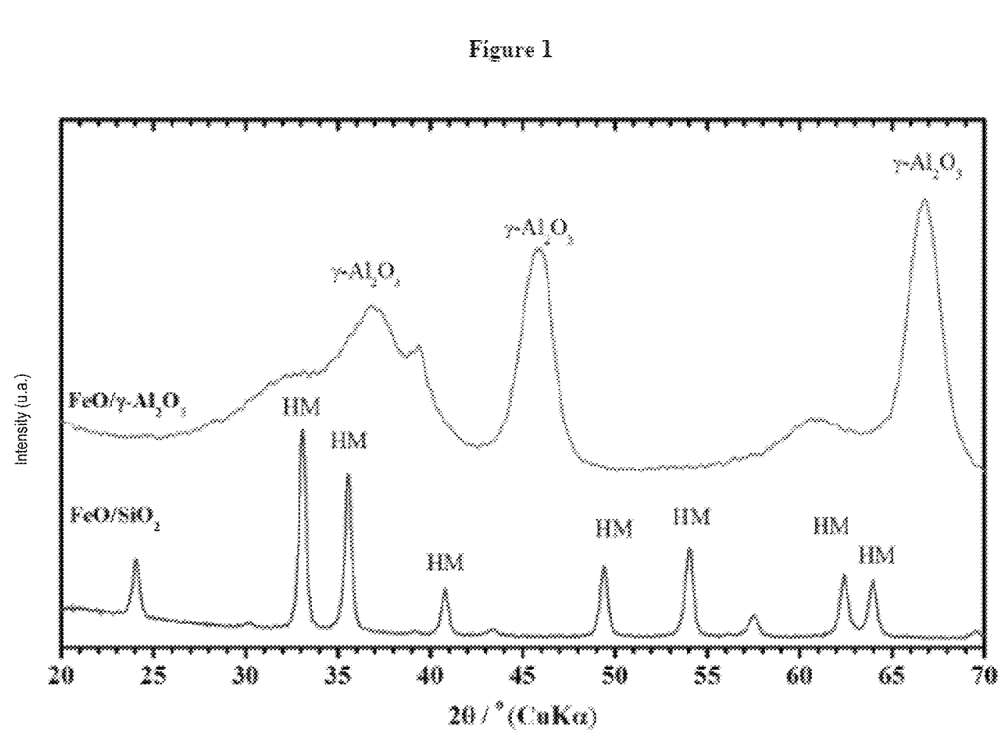
FIG. 1 contains the images obtained by transmission electron microscopy (TEM) in FeKα mode filtered from silica- and alumina-supported iron oxide-containing catalysts.

The images obtained by transmission electron microscopy (MET) of the FeO/Al$_2$O$_3$ material show that the iron oxide phase is widely dispersed in the support (FIGS. 1a and 1c). The iron oxide phase was detected only when images were taken in EF-TEM mode, taken at 708 eV (FIGS. 1b and 1d) and confirmed by the spectrum obtained via electron energy loss spectroscopy (Electron Energy Loss Spectroscopy—EELS) (FIG. 1e). The FeO/SiO$_2$ material shows iron oxide crystals and plates under the silica support that are ~50 nm in diameter and ~200 nm in length, respectively (FIGS. 1f and 1g).

Example 4—Characterization by X-Ray Diffraction (XRD)

Figure 2:
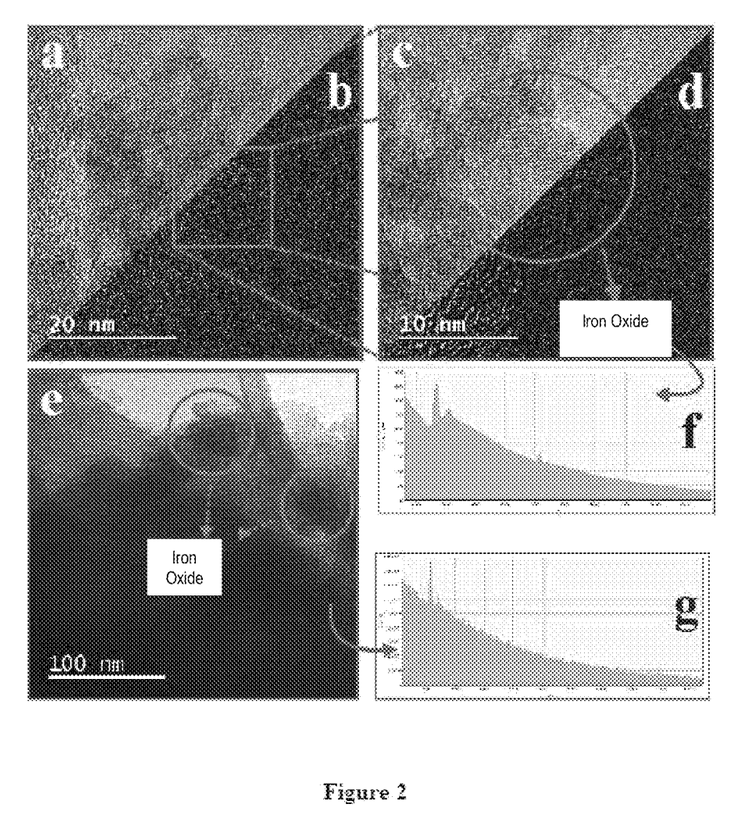
FIG. 2 contains the X-ray diffractograms of silica- and alumina-supported iron oxide-containing catalysts.

X-ray diffraction (XRD) data was collected for the synthesized catalysts in examples 1 and 2 with an XRD-700 diffractometer using CuKα radiation. The X-ray diffractograms of the FeO/SiO$_2$ and FeO/Al$_2$O$_3$ samples are shown in FIG. 2.

The reflections in the diffractogram of the FeO/SiO$_2$ sample are typical of the hematite phase (α-Fe$_2$O$_3$-HM). The SiO$_2$ support does not present a crystalline phase, and therefore is not detected in the XRD analysis. The broad base of all hematite reflections (HM) shows that the iron oxide crystals are on a nanometric scale. On the other hand, the iron oxide phase cannot be indexed in the diffractogram of the FeO/Al$_2$O$_3$ material due to the intense reflection of the poorly crystalline γ-Al$_2$O$_3$ phase of the support.

Example 5—Textural Properties and Acidity of Catalysts

The texture properties of the synthesized catalysts in examples 1 and 2 were determined by nitrogen adsorption at −196° C. in an Autosorb-1 Quantachrome system. The samples were degassed at 110° C. for 10 hours, and the specific area was calculated using the BET method (Brunauer-Emmett-Teller). The acidic sites were quantified by pyridine adsorption, followed by thermogravimetric analysis and Fourier-transform infrared spectroscopy (FTIR). The results of the textural and acidity analyzes are shown in the following table:

TABLE 1

Results of textural and acidity analyses for the catalysts in examples 1 and 2

| Catalyst | Fe content (%) | Specific area (m$^2$/g) | Total acidic sites (g$^{-1}$) |
|---|---|---|---|
| FeO/SiO$_2$ | 5.3 | 1340 | 3.81 × 10$^{19}$ |
| SiO$_2$ | 0.0 | 1450 | 1.07 × 10$^{20}$ |
| FeO/γ-Al$_2$O$_3$ | 4.5 | 192 | 7.61 × 10$^{19}$ |
| γ-Al$_2$O$_3$ | 0.0 | 230 | 2.05 × 10$^{20}$ |

With the build-up of iron oxide in the support, it is seen that the total number of available acidic sites decreases by an order of magnitude and that the alumina-supported catalyst has twice the number of acidic sites when compared to the silica-supported catalyst.

Example 6—Conversion Test for Glycerol-Containing Raw Material

In order to simulate the reaction process used in the industry, a system for continuous-flow reaction was set up. The reactions were conducted in a cylindrical reactor that is 54.0 cm long and with an internal diameter of 1.2 cm.

The heating was done in a split electric oven with three heating zones. The first heating zone was kept at 60° C. as a preheating zone, and the catalyst was positioned between the second and third heating zones. Blank tests (without catalyst) were carried out, and using the synthesized catalysts in examples 1 and 2. For the purpose of comparison, it was also used as a bulk hematite catalyst without dispersal in a support (α-Fe$_2$O$_3$-HM).

The tests were carried out with the second and third heating zones both at 150 and 200° C., to guarantee temperature homogeneity. Internal and external thermocouples recorded the temperature inside and outside the reactor, respectively.

The catalytic bed was filled with silicon carbide with 100-mesh granulometry. The iron oxide-containing catalyst was diluted in 9 mL of 60-mesh silicon carbide and positioned in the middle of the reactor, between the second and third heating zones, in order to obtain greater temperature homogeneity, occupying a real volume of 10.73 mL.

Before performing the reaction, the crude glycerin was filtered to remove solid particles. A container was filled with a mixture of crude glycerin and hydrogen peroxide solution in volume ratios of 1:2 and 1:1, and connected to the reaction vessel by a hose. Tests were carried out at two different concentrations of hydrogen peroxide, 35% v/v and 50% v/v.

The mixture was pumped in an upward flow using an HPLC pump, model AT2000 (Shimadzu) in order to obtain a weight hour space velocity (WHSV) of 3 h$^{-1}$. Tests were also carried out using twice the weight of the iron oxide-containing catalyst, and maintaining the flow rate of the glycerin-hydrogen peroxide mixture in order to obtain a weight hour space velocity (WHSV) of 1.5 h$^{-1}$. The resulting oxidized mixture passed through a condenser at 15° C., where the oxidation products were collected in a closed container.

Example 7—Analysis of the Products

The oxidized mixture was analyzed via gas chromatography coupled to a mass spectrometer (CG-MS). CG-MS analysis was performed using Agilent equipment, with HP-5MS column (5% polymethylphenylsiloxane), 30 m×250 μm×0.25 μm. The heating ramp was: initial temperature of 40° C. for 5 min, followed by heating to 140° C. at a rate of 5° C./min and kept at that temperature for 1 min. Then the temperature was increased to 290° C. at 20° C./min and maintained again for 1 min. The separated products were ionized via electron impact and analyzed in an Ion Trap analyzer.

The conversion was estimated using the analytical curve of glycerol in CG-MS by the following equation:

$$\frac{C}{\%} = \left(\frac{AC_p - AC_A}{AC_p}\right) \times 100 \times \text{Response Factor}$$

Where:
$AC_P$=chromatographic area of the standard; and
$AC_a$=chromatographic area of the sample.
The relative distribution of products was estimated according to the equation:

$$DP/\% = \frac{AC_i}{AC_t}$$

Where:
AC_i=chromatographic area of the product of interest; and
AC_f=sum of the chromatographic area of all oxidation products.

Selectivity was calculated in relation to the number of carbon moles entering and leaving the system, in accordance with:

$$S/\% = \frac{\text{No. of carbon moles from the product}}{\text{No. of carbon moles of converted glycerin}}$$

The main products formed in the tests performed were formic acid and a mixture of 1,3-dioxolan-4-methanol and 1,3-dioxan-5-methanol, hereinafter called "dioxanes."

Figure 3:
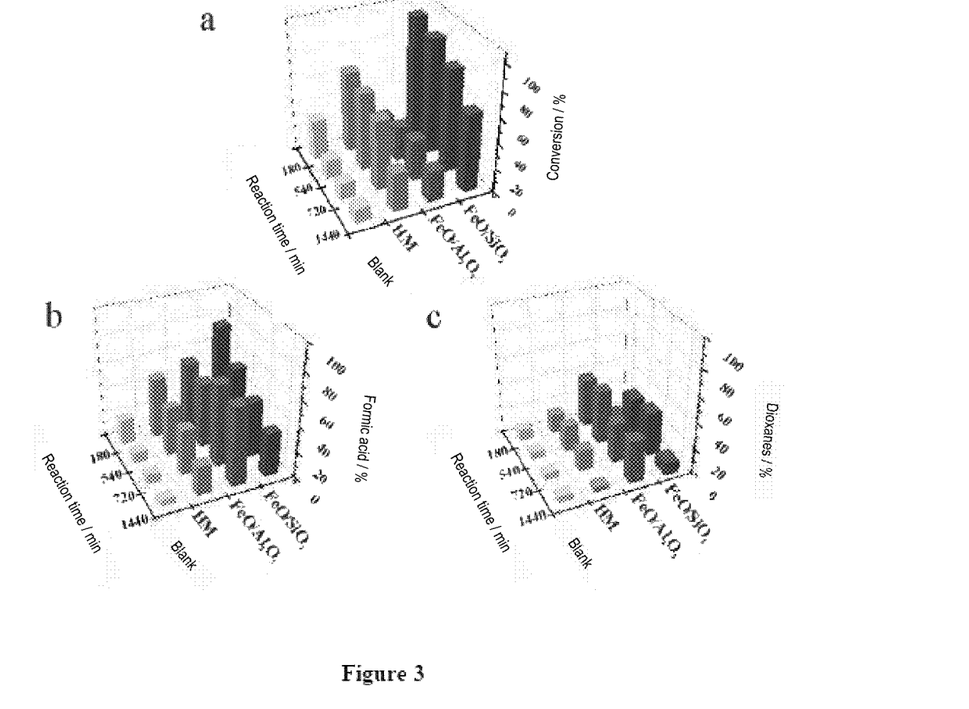
FIG. 3 contains a graph of the results of conversion (a) and distribution of the formic acid products (b) and dioxanes (c) as a function of the reaction time in tests carried out at 200° C. and at a weight hour space velocity (WHSV) of 3.0 $h^{-1}$.

As can be seen in FIG. 3, the alumina-support iron oxide-containing catalyst resulted in low conversions (from 20 to 30%), while bulk hematite (without dispersal in a support) resulted in an initial conversion of 40%, decreasing to 25% after 1440 min (FIG. 3a). Only by means of temperature, without the presence of a catalyst (blank test), was the system able to convert 15% of the crude glycerin. This result shows the importance of dispersing the active phase in a support in order to increase catalytic activity. Formic acid was also obtained without the presence of a catalyst, however the yield was low when compared to reactions in the presence of a catalyst.

Figure 4:
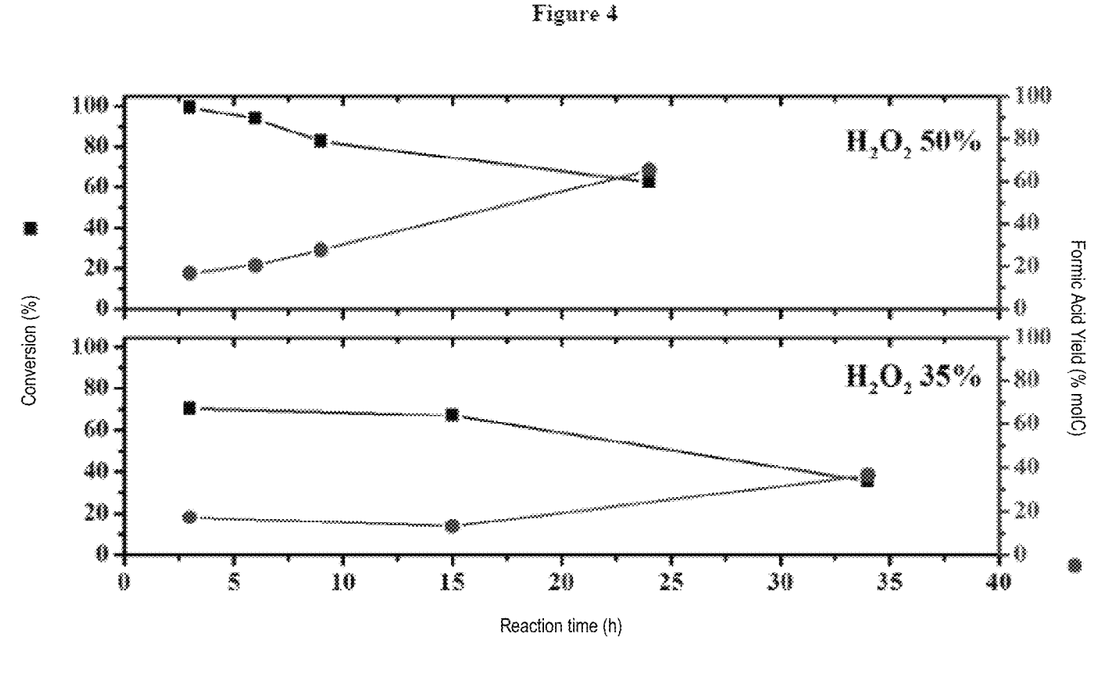
FIG. 4 contains a comparative graph of formic acid conversion and yield at different concentrations of hydrogen peroxide used for the silica-supported iron oxide-based catalyst in a test performed at 200° C. under weight hour space velocity (WHSV) of 3.0 $h^{-1}$.

As shown in FIG. 4, the distribution of products in the liquid phase was essentially the same when the concentration of the oxidizing agent solution was reduced from 50% v/v to 35% v/v and the working temperature was kept at 200° C. with the FeO/SiO_2 catalyst. Dilution of the oxidizing agent led to decreased conversion and yield to formic acid. However, there was a decrease in the generation of bubbles in the reaction line. A technical problem was observed upon the appearance of bubbles, which led to interruption of the flow by the HPLC pump used in pumping the reaction load to the reactor bed. When the flow is interrupted, it is necessary to discard the equivalent to the volume of the catalytic bed in order to exchange the entire interior load. It was also noted that it was easier to control the temperature of the entire system, since decomposition of $H_2O_2$ is exothermic. Thus, the decreased concentration of the oxidizing agent led to an increase in the safety and operability of the process.

It should be noted that the use of a volume ratio (crude glycerin):(hydrogen peroxide solution) of 1:1 with the 35% $H_2O_2$ solution provided a sufficient amount of water to prevent crystallization of sodium chloride (from crude glycerin) inside the reactor.

Figure 5:
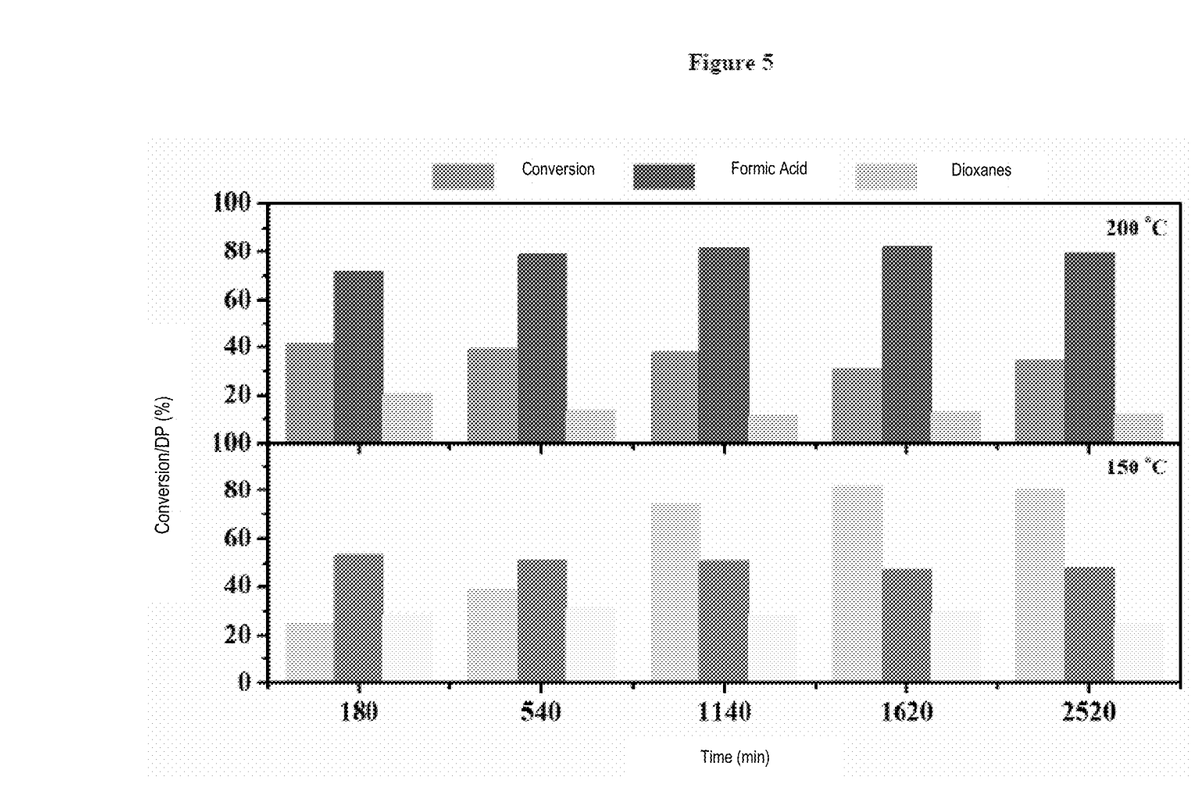
FIG. 5 contains a comparative graph of the product conversions and distribution in tests performed using a silica-supported iron oxide-containing catalyst at temperatures of 200 and 150° C. under weight hour space velocity (WHSV) of 3.0 $h^{-1}$.

The comparative graphs in FIG. 5 show that both at 200° C. and 150° C., the majority product was formic acid, followed by dioxanes. As the rate of formic acid increases, the rate of dioxanes decreases. The "other" products are basically comprised of hydroxypropanone (HPN), acetic acid, 1,3-butadiene and some molecules not identified in the GC-MS.

Figure 6:
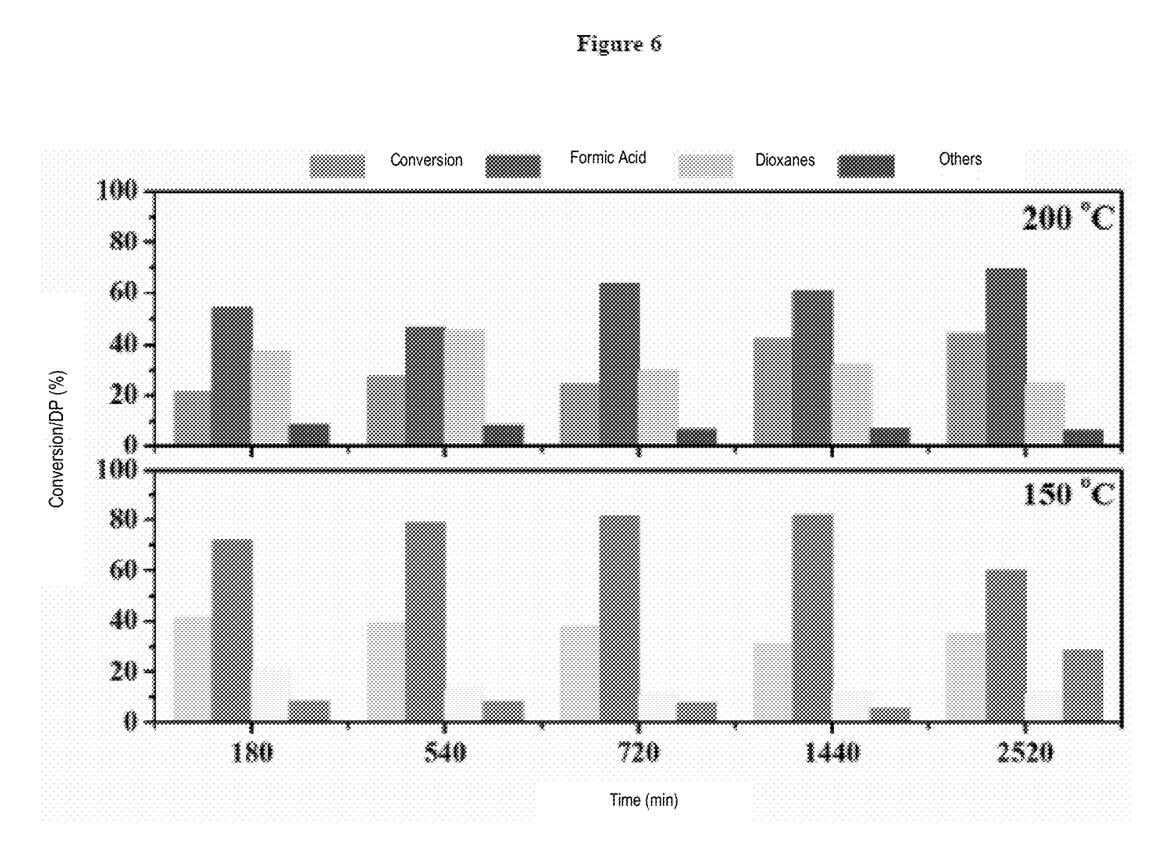
FIG. 6 contains a comparative graph of the product conversions and distribution in tests performed using an alumina-supported iron oxide-containing catalyst at temperatures of 200 and 150° C. under weight hour space velocity (WHSV) of 3.0 $h^{-1}$.

The comparative graphs in FIG. 6 show that the FeO/Al_2O_3 catalyst resulted in lower conversion rates, compared to the FeO/SiO_2 catalyst. However, the alumina-supported catalyst is more stable for the entire time it was in the catalytic bed. In the alumina-supported catalyst, formic acid was obtained in higher yields both at 200 and at 150° C. when compared to the silica-supported catalyst. The system using FeO/Al_2O_3 resulted in higher yield of formic acid in the mildest experimental conditions, at 150° C. and 1:1 glycerol:$H_2O_2$ molar ratio. There was an increase in the "other" products obtained, and a decrease in that of dioxanes and formic acid at the end of 2520 min. A loss of catalytic activity of the FeO/Al_2O_3 catalyst at 150° C. was also seen, which loss was not seen at 200° C.

Figure 7:
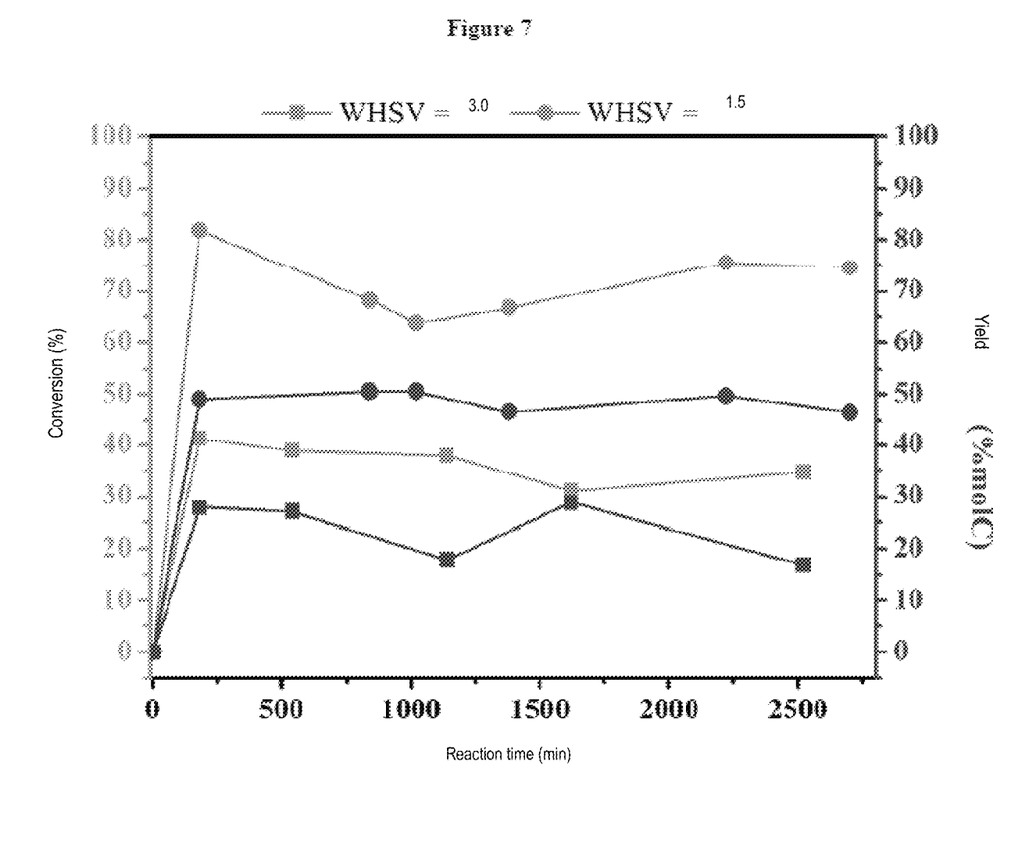
FIG. 7 contains a comparative graph of formic acid conversions and yield in tests performed using an alumina-supported iron oxide-containing catalyst under weight hour space velocities (WHSV) of 3.0 $h^{-1}$ and 1.5 $h^{-1}$, at a temperature of 150° C.

Finally, from the results shown in FIG. 7, it can be concluded that the two-fold increase in catalyst load or the decrease in WHSV led to a two-fold increase in the crude glycerin conversion rate, and also to the yield of formic acid in the same proportion.

The description provided up to this point regarding the purpose of the present invention should be considered only as a possible embodiment or embodiments, and any particular characteristics introduced herein should be understood only as something that has been written to facilitate comprehension. The description, therefore, cannot in any way be considered as limiting the invention, which is limited to the scope of the following claims.

The invention claimed is:

1. Glycerol A glycerol selective oxidation process, comprising the steps of:
   (a) feeding a glycerol-containing raw material and an oxidizing agent into a reaction vessel containing an iron oxide-containing catalyst;
   (b) putting the glycerol-containing raw material, the oxidizing agent, and the iron oxide-containing catalyst in contact at a temperature in the range of 100 to 350° C., forming an oxidized mixture;
   wherein the majority product of the oxidized mixture is formic acid.

2. The process of claim 1, wherein the content of formic acid in the oxidized mixture is in the range of 40 to 90% by weight, based on the sum of the weights of the oxidation products contained in the oxidized mixture.

3. The process of claim 1, wherein the glycerol-containing raw material and the oxidizing agent are mixed before being fed into the reaction vessel.

4. The process of claim 1, wherein the glycerol-containing raw material and the oxidizing agent are fed into the reaction vessel in a volume ratio of (glycerol-containing raw material):(oxidizing agent) in the range of 1:1 to 1:5.

5. The process of claim 1, wherein the oxidizing agent is selected from the group consisting of hydrogen peroxide, oxygen, ozone, or solutions thereof.

6. The process of claim 1, wherein the oxidizing agent is a solution of hydrogen peroxide in a concentration in the range of 10 to 50% v/v, based on the total volume of the solution.

7. The process of claim 1, wherein the glycerol content in the glycerol-containing raw material is in the range of 30 to 100% by weight.

8. The process of claim 1, wherein the process is carried out in a continuous regime.

9. The process of claim 8, wherein it is carried out under weight hour space velocity (WHSV) in the range of 0.5 to 10 h−1.

10. The process of claim 8, wherein the reaction vessel is selected from the group consisting of a fixed bed reactor, fluidized bed reactor, and mud bed reactor.

11. The process of claim 1, wherein it further comprises a product recovery step (c), in which the oxidized mixture is subjected to a process selected from simple distillation, fractional distillation, simple condensation, fractional condensation, or a combination thereto.

12. The process of claim 1, wherein it comprises an initial pre-treatment step of the glycerol-containing raw material.

13. The process of claim 12, wherein the pre-treatment of the glycerol-containing raw material comprises a step selected from the group consisting of hydrolysis, filtration, physisorption, chemisorption, distillation, decantation, neutralization, refining, or combinations thereof.

14. The process of claim 1, wherein the iron oxide of said iron oxide-containing catalyst is dispersed in a catalytic support selected from the group consisting of silica, alumina, activated carbon, diatomaceous earth, pumice, and zeolite.

15. The process of claim 1, wherein said iron oxide-containing catalyst has iron content in the range of 1 to 20% by weight.

16. The process of claim 1, wherein the iron oxide-containing catalyst is previously diluted in an inert solid diluent in a volume ratio of catalyst:diluent in the range of 1:1 to 1:20.

17. The process of claim 16, wherein the inert solid diluent is selected from the group consisting of silica, alumina, silicon carbide, glass beads, quartz chips, activated carbon, and pumice.

18. The process of claim 2, wherein the glycerol-containing raw material and the oxidizing agent are mixed before being fed into the reaction vessel.

* * * * *